(12) United States Patent
Hoffnagle et al.

(10) Patent No.: US 11,592,388 B2
(45) Date of Patent: Feb. 28, 2023

(54) CLUTTER AVOIDANCE IN WIDE-BAND CAVITY RING-DOWN DATA ACQUISITION

(71) Applicant: Picarro, Inc., Santa Clara, CA (US)

(72) Inventors: John A. Hoffnagle, San Jose, CA (US); Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 334 days.

(21) Appl. No.: 16/714,536

(22) Filed: Dec. 13, 2019

(65) Prior Publication Data

US 2021/0181092 A1    Jun. 17, 2021

(51) Int. Cl.
| | | |
|---|---|---|
| *G01N 21/31* | (2006.01) | |
| *G01J 3/42* | (2006.01) | |
| *G01N 33/00* | (2006.01) | |

(52) U.S. Cl.
CPC ............... *G01N 21/31* (2013.01); *G01J 3/42* (2013.01); *G01N 33/006* (2013.01); *G01N 33/0047* (2013.01); *G01N 33/0059* (2013.01)

(58) Field of Classification Search
CPC .. G01N 33/0059; G01N 33/006; G01N 21/31; G01N 3/42; G01N 33/0047; G01N 21/39; G01N 2021/391; G01J 3/027; G01J 3/42
See application file for complete search history.

(56) References Cited

U.S. PATENT DOCUMENTS

2016/0011101 A1*  1/2016  Ognibene ................. G01J 3/42
                                                                      356/437

FOREIGN PATENT DOCUMENTS

WO    WO-2021079184 A1 *  4/2021  ............. G01J 3/443

OTHER PUBLICATIONS

Cossel et al., "Gas-phase broadband spectroscopy using active sources: progress, status, and applications", 2017, J. Opt. Soc. Am. B 34, 104-129.
Ycas et al., "Mid-infrared dual-comb spectroscopy of volatile organic compounds across long open-air paths", 2019, Optica vol. 6, No. 2.

* cited by examiner

*Primary Examiner* — Dominic J Bologna
*Assistant Examiner* — Amanda Merlino
(74) *Attorney, Agent, or Firm* — Lumen Patent Firm (57) ABSTRACT

Improved optical absorption spectroscopy of species having broad spectral features is provided by choosing frequencies to cover the spectral feature(s) of interest, where the frequencies are slightly adjusted as needed to avoid narrow spectral features from interfering chemical species (i.e., clutter). The resulting clutter avoidance provides improved optical spectroscopy of species having broad spectral features.

18 Claims, 7 Drawing Sheets

CLUTTER AVOIDANCE IN WIDE-BAND CAVITY RING-DOWN DATA ACQUISITION

FIELD OF THE INVENTION

This invention relates to spectroscopic analysis.

BACKGROUND

Ultra-sensitive spectroscopic detection (e.g., via cavity ring-down spectroscopy (CRDS)) of trace gas species in gas samples depends significantly on the kind of gas analyte being detected. If the analyte of interest is a small molecule, it is usually possible to find a small (i.e., sub-nm) wavelength/frequency range that includes distinctive spectral features of the analyte of interest without undue interference from other species.

However, other analytes have broad, continuous absorption features. Examples of practical importance include volatile organic compounds (VOCs) such as alkanes heavier than methane, aldehydes, aromatics (e.g. BTEX (benzene, toluene, ethylbenzene and xylene)), halocarbons including propellants and refrigerants, solvents, etc. All these molecules have spectral features showing distinctive differences which are only visible when absorption is sampled over a wavelength range of at least several nanometers.

In typical applications, VOCs are to be detected in normal ambient air. In this case, one has to distinguish infrared absorption due to the compounds of interest from absorption due to the small molecules that make up normal air. The most important infrared absorbers in ambient air are methane (approximately 2 ppm in clean air), carbon dioxide (approximately 400 ppm), and water vapor (variable over a wide range, from a few ppm to several percent). These molecules also have distinctive spectra which, for typical conditions of temperature and pressure in ring-down spectroscopy, have a very large number (hundreds to thousands, depending on where one chooses to draw an intensity cut-off) of discrete, spectrally narrow lines. This multitude of sharp, strong absorption lines, which obscures the details of the VOC spectra of interest to us, is what we call "clutter".

Figure 1:
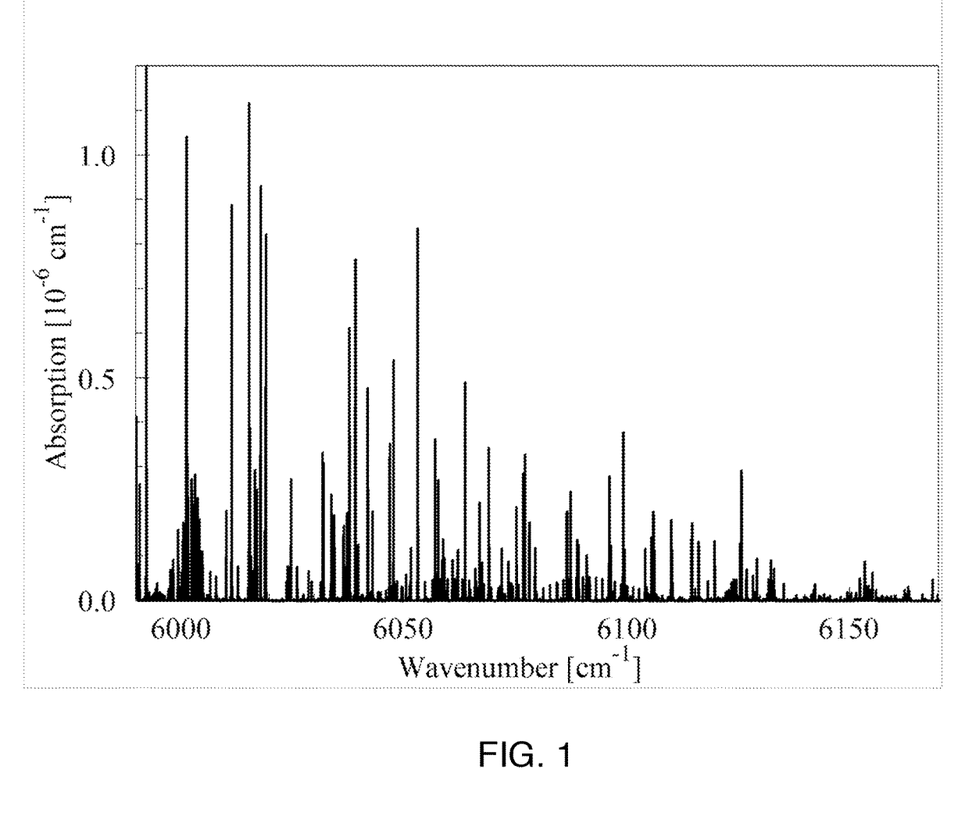
FIG. 1 is a HITRAN simulation of an exemplary clutter spectrum.

The clutter problem is illustrated graphically in FIG. 1, which shows a Hitran simulation of the absorption of an air sample from about 6000 to about 6150 cm$^{-1}$ (a 49 nm wavelength range). It is important to note that the intrinsic sensitivity of state of the art CRDS instruments is on the order of $10^{-11}$ cm$^{-1}$, or $10^{-5}$ times the absorption of the strongest lines in this figure, and of course it is desired to measure VOC absorption with this level of sensitivity. It is therefore necessary to reject the contribution of clutter to the total absorption spectrum to an extremely high degree.

One way to deal with clutter is by careful modeling of the absorption by small molecules in the context of a global modeling or fitting procedure that includes both clutter and absorption by the larger molecules of interest. In the case of water vapor and $CO_2$, it is possible to find analytic representations of the individual absorption lines by applying the basic physics of molecular line shape theory, giving us a mathematical model of the strongest molecular absorption lines in the frequency range of interest. With this model we can deal with much of the clutter in the spectra we expect to acquire from real air samples. Methane is more difficult to describe from first principles, but we can still use empirical methods to construct a concise spectral model from our careful measurements of pure methane. But modeling also has its limitations.

The huge dynamic range of CRDS measurements, covering five orders of magnitude from the sensitivity limit of the apparatus to the size of the largest absorption features, places extreme requirements on the accuracy of the spectral modeling. Modeling can go far in dealing with clutter, but it will be difficult to account for small molecule absorption at the very high level of precision which we expect will be necessary for the best possible VOC detection.

The difficulty in modeling the clutter is compounded by the following real world challenges:

1) Collecting a spectrum takes a finite amount of time. If the concentration of the clutter compounds changes during the spectral collection time, the time-varying absorption from the clutter will be mapped into apparent wavelength variability that will be difficult for the model to capture. A similar effect can be caused by pressure fluctuations.

2) The clutter spectrum has not only high absorption loss, but a large derivative with respect to wavelength. This means that even small wavelength uncertainty in the recorded spectrum is mapped into a relatively large absorption uncertainty, which further limits the accuracy of the modeling.

Accordingly, it would be an advance in the art to provide an improved approach for dealing with clutter.

SUMMARY

This work provides a strategy which we refer to as "clutter avoidance." It starts with the observation that, although absorption lines due to small molecules are present throughout the wavelength region of interest to us, these lines are narrow under the conditions of our measurements, and consequently there is considerable frequency space between the lines of clutter.

Figure 2:
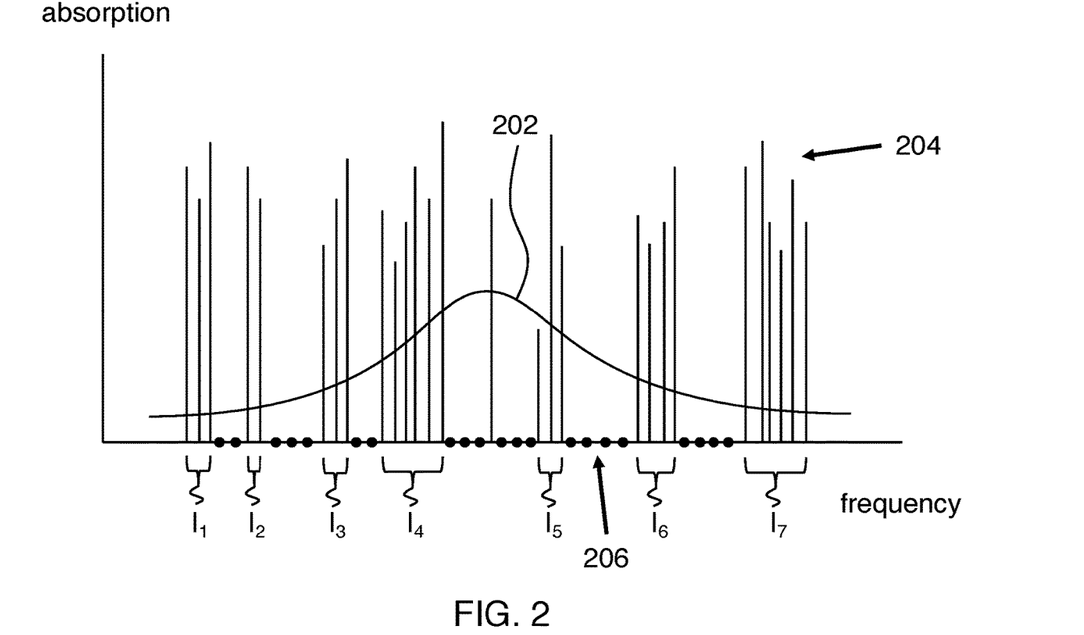
FIG. 2 shows a first example of clutter avoidance.

This situation is schematically shown on FIG. 2, where 202 is a spectral feature of an analyte of interest, and 204 is the clutter. Importantly, this figure is not to scale, and the magnitude of analyte feature 202 relative to clutter 204 is greatly exaggerated. This emphasizes, once again, the difficulty of dealing with clutter.

This means that we can define a set 206 of special frequencies (black dots on FIG. 2) covering the entire range of interest, and which have the property that absorption due to small molecules at these special frequencies is much less than it would be for frequencies chosen at random. The notion of acquiring ring-down data at frequencies for which the broad-band, nearly continuous absorption due to large molecules is present but absorption due to the narrow lines of small molecules is nearly absent is what we call clutter avoidance.

Accordingly, an embodiment of the invention is a method for performing spectroscopic analysis of a sample with an analysis instrument, where the method includes:

1) for a predetermined frequency range and one or more predetermined clutter species, automatically determining one or more avoidance intervals (e.g., $I_1$, $I_2$, $I_3$, $I_4$, $I_5$, $I_6$, $I_7$ on FIG. 2) in the predetermined frequency range; and 2) performing spectroscopy of one or more analyte species in the sample at a first set of frequencies (e.g., set 206 on FIG. 2) that are all outside the avoidance intervals to provide a first set of data points. Here the analyte species are distinct from the clutter species.

Two aspects of the clutter avoidance idea should be emphasized here. First, it is not an alternative to careful modeling, as described above, but rather complementary to modeling. By minimizing the absorption due to clutter in our acquired data sets, we relax, but in generally cannot eliminate, the requirement for modeling precision that is needed to account for small-molecule absorption at any absolute level of absorption. The remaining absorption observed at the clutter avoidance frequencies is due to off-resonance absorption far in frequency from the center of the strong clutter causing lines. The off-resonance absorption depends most strongly on
1) the concentrations of the compounds that contribute to clutter;
2) the sample pressure; and
2) the composition of the background gas matrix (because different gases cause different amounts of line broadening).

Therefore, it is preferred to create a single spectroscopic data collection scheme that provides a broadband clutter avoidance spectrum but that also measures targeted features of the clutter compounds. Analysis of this hybrid spectrum can be used to constrain the gas pressure and sample gas composition, which can in turn to improve the analysis of the clutter avoidance part of the spectrum (e.g., provide improved sensitivity to the one or more analyte species). There is of course a practical trade off which must be made between these two conflicting goals of constraining the clutter spectrum and delivering a spectrum that is minimized in clutter.

Figure 3:
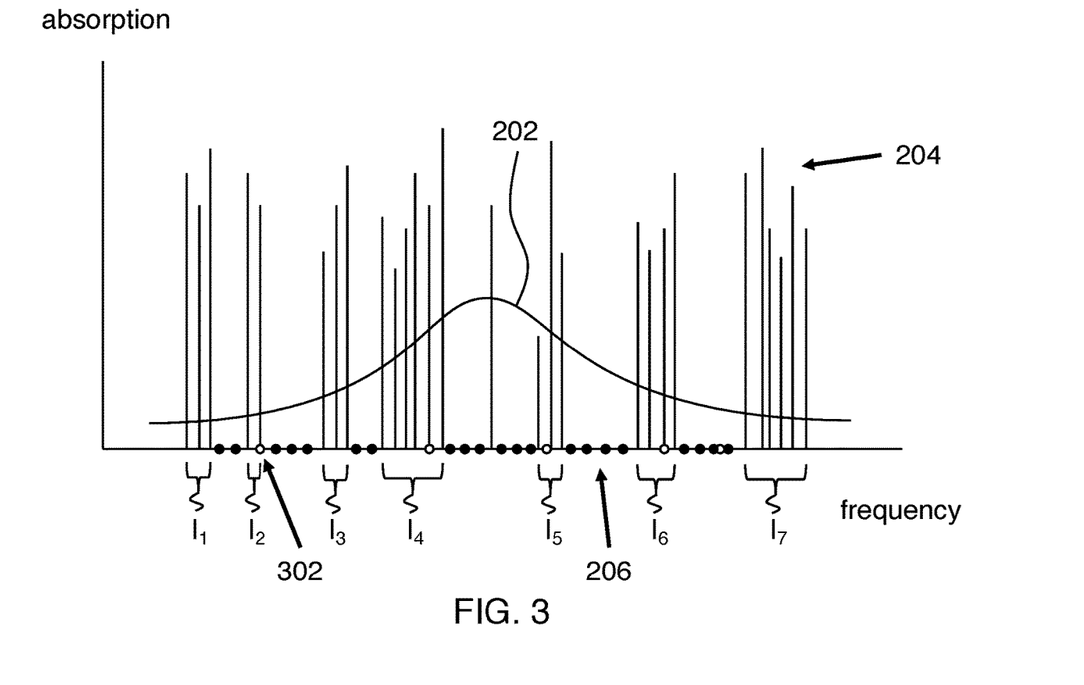
FIG. 3 shows a second example of clutter avoidance.

FIG. 3 schematically shows this idea. Here measurements are also performed at a second set 302 of frequencies (open circles on the figure). Typically, frequencies in the second set of frequencies are within the avoidance intervals to efficiently sample the clutter spectrum, but they can also be outside the avoidance intervals (e.g., the open circle between $I_6$ and $I_7$ on FIG. 3). As indicated above, the purpose of this second set of data points is to provide improved spectral fitting of the off-resonance clutter features in the first set of data points.

This improved spectral fitting can take many forms. For example, either individually or in any combination:
1) a reduction in one or more concentration uncertainties of one or more clutter species in the sample;
2) a reduction in one or more isotopologue abundance uncertainties of one or more clutter species in the sample;
3) a spectral measurement of pressure of the sample;
4) a spectral measurement of temperature of the sample;
5) a spectral measurement of a background matrix gas composition of the sample—here concentrations of one or more constituents of the background matrix gas composition can be determined by their effect on spectral fitting of other chemical species using the first and/or second set of data points; and
6) a reduction in uncertainties of one or more assigned frequency values in the first and/or second sets of data points. One example of such a process might include the measurement of one or more clutter peaks in the avoidance interval. By measuring the apparent line centers of these specific peaks and comparing the peaks to the known line centers, one may derive a transformation to convert the spectrometer frequency scale into a corrected frequency scale, which can then be applied to the spectral data associated with the first set of frequencies to improve the modeling of the clutter species and/or the analysis of the broadband analyte spectra.

Second, the implementation of clutter avoidance is closely connected to the special data acquisition capabilities of preferred CRDS spectrometers. Many implementations of infrared absorption spectroscopy using wavelength modulation or frequency modulation sweep the laser frequency in a continuous fashion across the range of interest while recording the light transmitted through the sample. Measurements conducted that way record whatever absorption is present in the sample and it is difficult if not impossible to avoid acquiring a cluttered data set (though of course one is free to ignore any data points one wishes in the subsequent analysis). In contrast, CRDS is a step-by-step procedure in which cavity loss is measured at a sequence of distinct optical frequencies. Preferably, the CRDS instrument employed provides complete control of optical frequency for each ring-down event, without regard to whatever ring-downs have come before. With such an instrument, we are therefore free to acquire data only at the frequencies of most value for our intended VOC measurement, and need not waste any time acquiring data at frequencies for which absorption is dominated by clutter.

DETAILED DESCRIPTION

This section describes an experimental realization of the clutter avoidance idea for data acquisition in the frequency range 5995 $cm^{-1}$-6170 $cm^{-1}$, where there are strong and distinctive features of many hydrocarbon molecules. The principles are broadly applicable to other optical frequencies, while many details could be changed without affecting the basic design.

The first requirement is a criterion to distinguish those frequencies subject to clutter from those which we may regard as clutter-free. This distinction can be based on high-resolution spectra of the three important small molecules in ambient air. In this work, spectra were acquired from samples of 10 ppm methane, 3000 ppm $CO_2$, and 4.23% water vapor. These are higher concentrations than we would expect to see in most ambient air samples. The spectra were all acquired at a pressure of 140 Torr and a temperature of 80° C. Frequency resolution was approximately 0.005 $cm^{-1}$, which is considerably less than the width of isolated lines for these molecules under the sample conditions. An optical frequency was flagged as being affected by clutter if absorption due to any of the three species considered here (from the raw absorption spectra after background subtraction) exceeded a threshold value of 10 ppb/cm. The justification for this threshold is that it is about 1000 times greater than the intended detection limit for absorption, so that spectral modeling of residual absorption only has to be precise to about 1 part in 1000 to completely account for small molecule absorption in our spectra, and modeling at this level of precision seems quite feasible. With this choice of threshold, 33% of the frequencies sampled in the full spectral region were flagged as subject to clutter. A separate processing step identified contiguous regions of flagged frequencies, producing a list of avoidance intervals (530 intervals in this implementation) affected by clutter. More generally, we provide spectral data of the one or more predetermined clutter species at a set of reference frequencies in the predetermined frequency range. This can be done by measurements as described above, and/or by consulting published spectral data.

More generally, the automatically determining one or more avoidance intervals in the predetermined frequency range preferably includes:
1) performing optical absorption spectroscopy of a reference sample including the one or more predetermined clutter species at a set of reference frequencies in the predetermined frequency range—here the spacing of the reference frequencies is preferably less than a full-width half maximum line width of any spectral feature of any of the predetermined clutter species;
2) automatically flagging reference frequencies having clutter absorption values greater than a predetermined threshold; and
3) automatically defining the avoidance intervals as contiguous sets of flagged reference frequencies.

The next step is to select the set of frequencies at which to measure ring-downs. This can be specified in a scheme, which is a master file controlling the data acquisition. Many options are possible, depending on the application for which the analyzer is to be used. For a general-purpose implementation, it makes sense to cover the entire spectral range of the ring-down instrument with approximately uniform spectral coverage. The number of distinct frequencies in the scheme is an important choice—more frequencies provide finer spectral coverage but take more time to acquire. Another important consideration is that it is generally highly desirable to measure ring-downs at frequencies which are all separated by integer multiples of the ring-down cavity free spectral range (FSR). This means that the mechanical length of the cavity stays the same for all ring-downs, which has two advantages: there is no need to move any cavity mirrors, which would slow down the data acquisition; and the FSR is very stable and can be measured very well, so that constraining the ring-down frequencies to lie on an FSR-spaced comb produces a spectrum with an extremely accurate frequency axis. The FSR is different for every ring-down cavity, due to small variations in the construction of the cavities. Consequently, the scheme of ring-down frequencies is preferably uniquely tailored to each individual ring-down cavity.

Figure 4A:
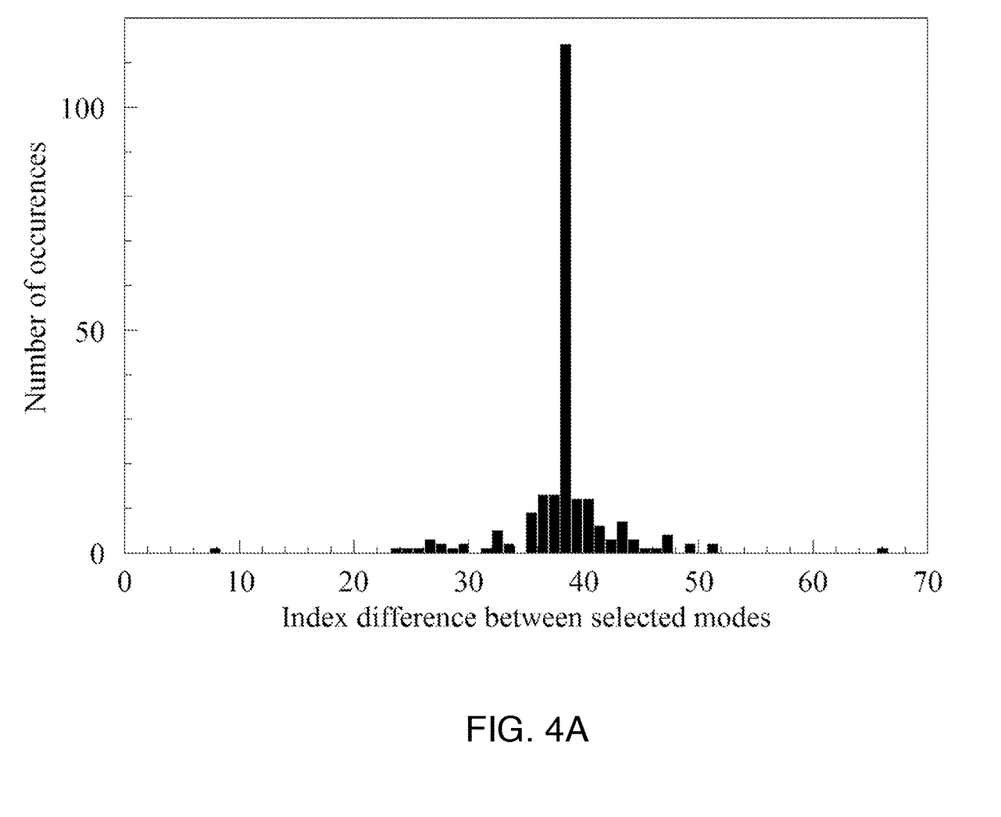
FIG. 4A is an exemplary histogram of frequency spacing in practicing clutter avoidance.
Figure 4B:
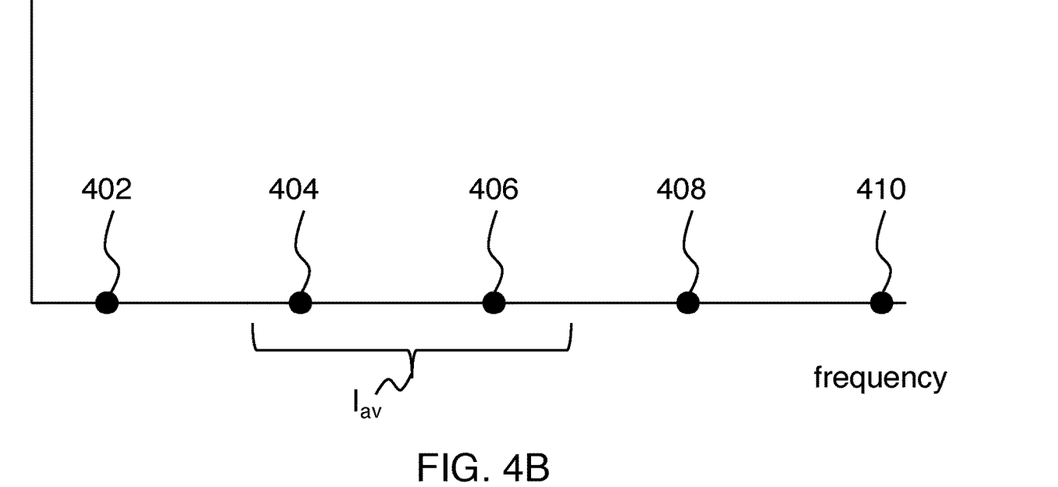
FIGS. 4B-C show operation of an exemplary method for selecting frequencies to avoid clutter.
Figure 4C:
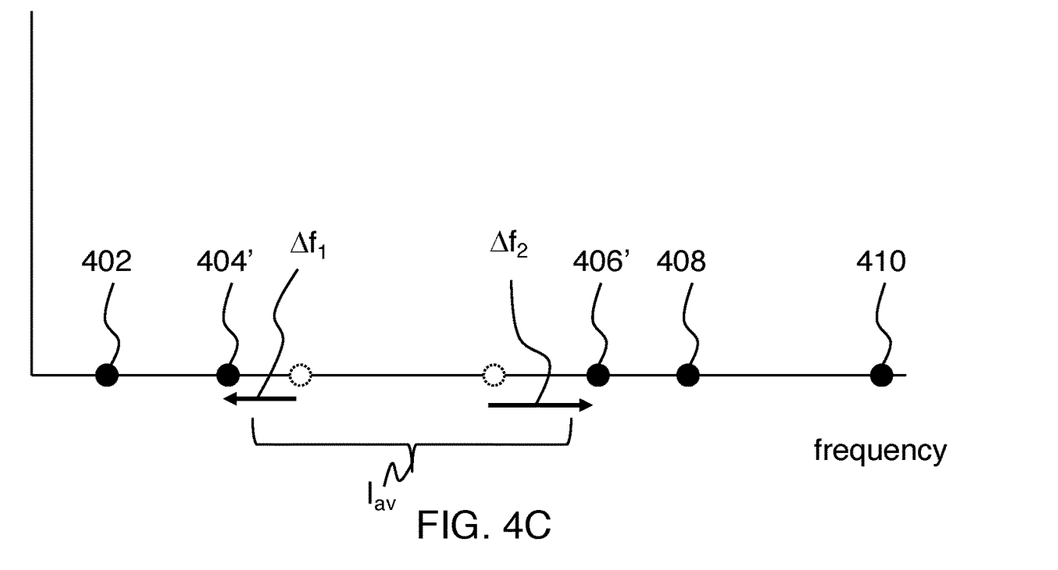

A suitable set of ring-down frequencies can be computed for each analyzer by the following algorithm.
1) Select minimum and maximum frequencies, $v_{min}$ and $v_{max}$, as well as one reference or target frequency $v_0$, which serves to establish an absolute frequency scale.
2) Select the number of frequencies N in the scheme.
3) Look up the FSR from the instrument calibration and compute a nominal separation between ringdown frequencies equal to the FSR times the integer part of the quantity $(v_{max}-v_{min})/(N\,FSR)$.
4) Construct a set of preliminary ring-down frequencies spaced by the nominal separation frequency and including the reference frequency $v_0$.
5) For each preliminary frequency defined in step 4, check the list of avoidance intervals to determine if the preliminary frequency lies in an avoidance interval. If not, then it is retained in the final scheme. If the preliminary frequency does lie in an avoidance interval, then find which edge of the avoidance interval is closest to the preliminary frequency and shift the preliminary frequency by an integer times the FSR, so that it lies just outside that avoidance interval. This shifted frequency becomes part of the final scheme. FIGS. 4B-C schematically show this step. Here lay is the relevant avoidance interval, and 402, 404, 406, 408 and 410 are evenly spaced preliminary frequencies. The final scheme includes frequencies 404' and 406' shifted from 404 and 406 by $\Delta f_1$ and $\Delta f_2$ respectively. As indicated above, $\Delta f_1$ and $\Delta f_2$ are preferably integer multiples of the CRDS instrument cavity FSR.

Somewhat more generally, the first set of frequencies can be determined by:
1) providing values for minimum frequency ($v_{min}$), maximum frequency ($v_{max}$), and number of frequencies to sample (N) to define a sampled frequency range;
2) automatically computing a nominal frequency separation from $v_{min}$, $v_{max}$, and N;
3) automatically approximating the nominal frequency separation with a multiple of a free spectral range (FSR) of an optical cavity of the cavity ring-down spectroscopy instrument to provide a frequency spacing $\Delta v$;
4) automatically determining a set of preliminary frequencies to cover the sampled frequency range with a comb of frequencies spaced by $\Delta v$ and including a reference frequency $v_0$;
5) automatically adjusting frequencies in the set of preliminary frequencies to avoid the avoidance intervals to provide the first set of frequencies.

The automatically adjusting frequencies in the set of preliminary frequencies preferably includes, for each preliminary frequency inside an avoidance interval: automatically shifting the preliminary frequency by a multiple M of the FSR to move it outside any avoidance interval, where M is minimized individually for each shifted frequency.

It is surely possible to find other ways to define a set of frequencies that avoid the regions affected by clutter, but this method gives a scheme with reasonably uniform frequency coverage.

Example: A specific scheme was prepared in this way for an experimental CRDS analyzer. The frequency range was 5995 cm$^{-1}$-6170 cm$^{-1}$ and N was chosen to be 220, giving a nominal frequency separation of 38 cavity modes between ring-down frequencies. It is interesting to see how far the ring-down frequencies in the final scheme had to be adjusted from the preliminary scheme in order to avoid the cluttered frequency regions. FIG. 4A shows a histogram of the separation between adjacent ring-down frequencies, in units of FSR, for the final clutter-avoiding scheme. About half the ring-down frequencies in the final scheme are spaced from their neighbors by the nominal 38 modes, and most of the rest are displaced by only a few modes from this nominal spacing. Consequently, the frequency sampling over this range is close to uniform, as desired.

Figure 5:
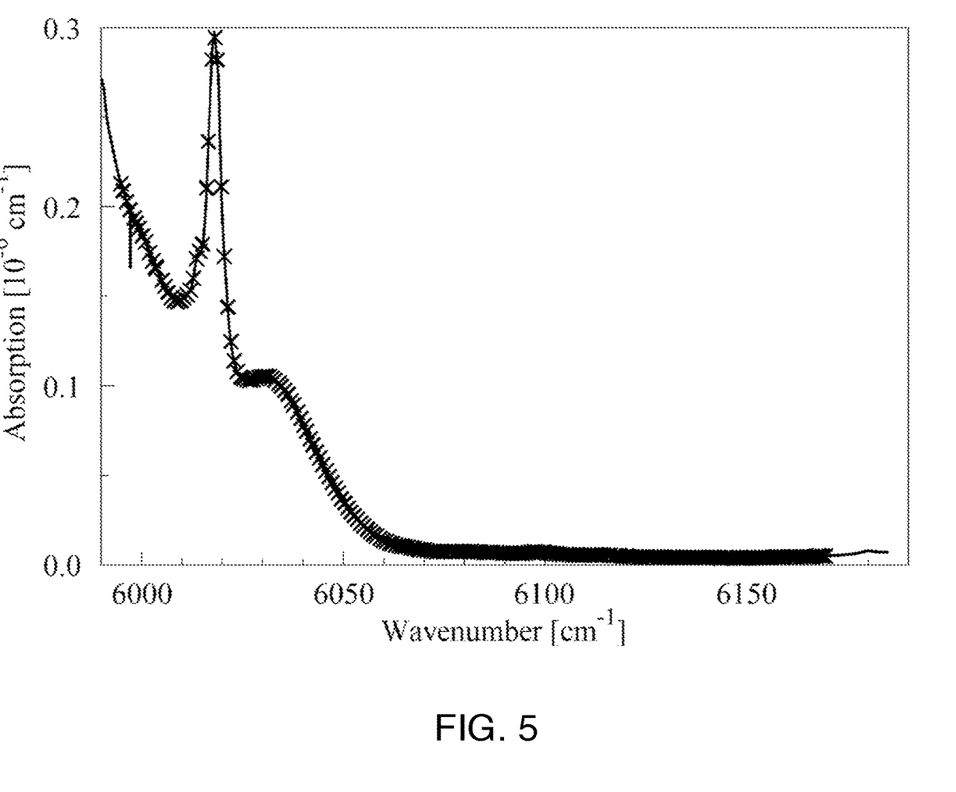
FIG. 5 is an exemplary absorption spectrum having broad spectral features as measured using clutter avoidance.

Another way to view the scheme generated in this way is to look at how it samples a typical organic absorption spectrum. FIG. 5 shows the complete spectrum of 1,1-difluoroethane (a refrigerant and spray-can propellant) together with the set of ring-down frequencies belonging to the clutter-avoiding scheme. The reason for looking at this specific fluorocarbon is that its spectrum has a spiked feature that is sharper than what one sees in most other VOCs. If the scheme were too irregular, then conceivably some of the characteristic shape of the absorption spectrum could be missed. In fact, the clutter-avoiding scheme gives good coverage of all the distinctive spectral features of this molecule. There is clearly adequate information to resolve the fine details of the spectrum.

Finally, we show how clutter avoidance affects spectra acquired with room air, in the case of this specific example. An experimental CRDS analyzer was programmed to acquire data sets using the scheme described above and, for comparison, using a scheme with approximately the same number of frequencies on a perfectly regular frequency grid, i.e. without any attempt to avoid clutter. The analyzer sampled air from a production floor, including nighttime periods when there was no activity on the floor as well as workday periods when the area was busy.

Figure 6A:
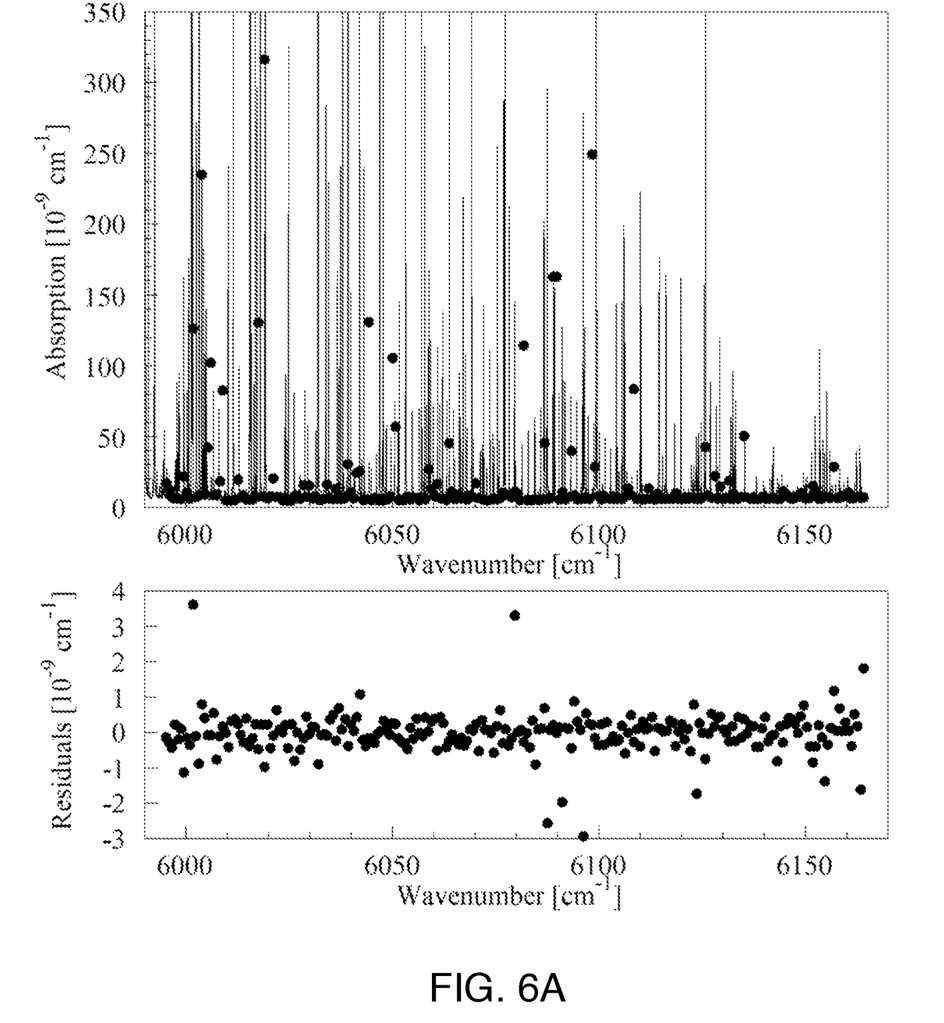
FIGS. 6A-B provide a further example of clutter avoidance.
Figure 6B:
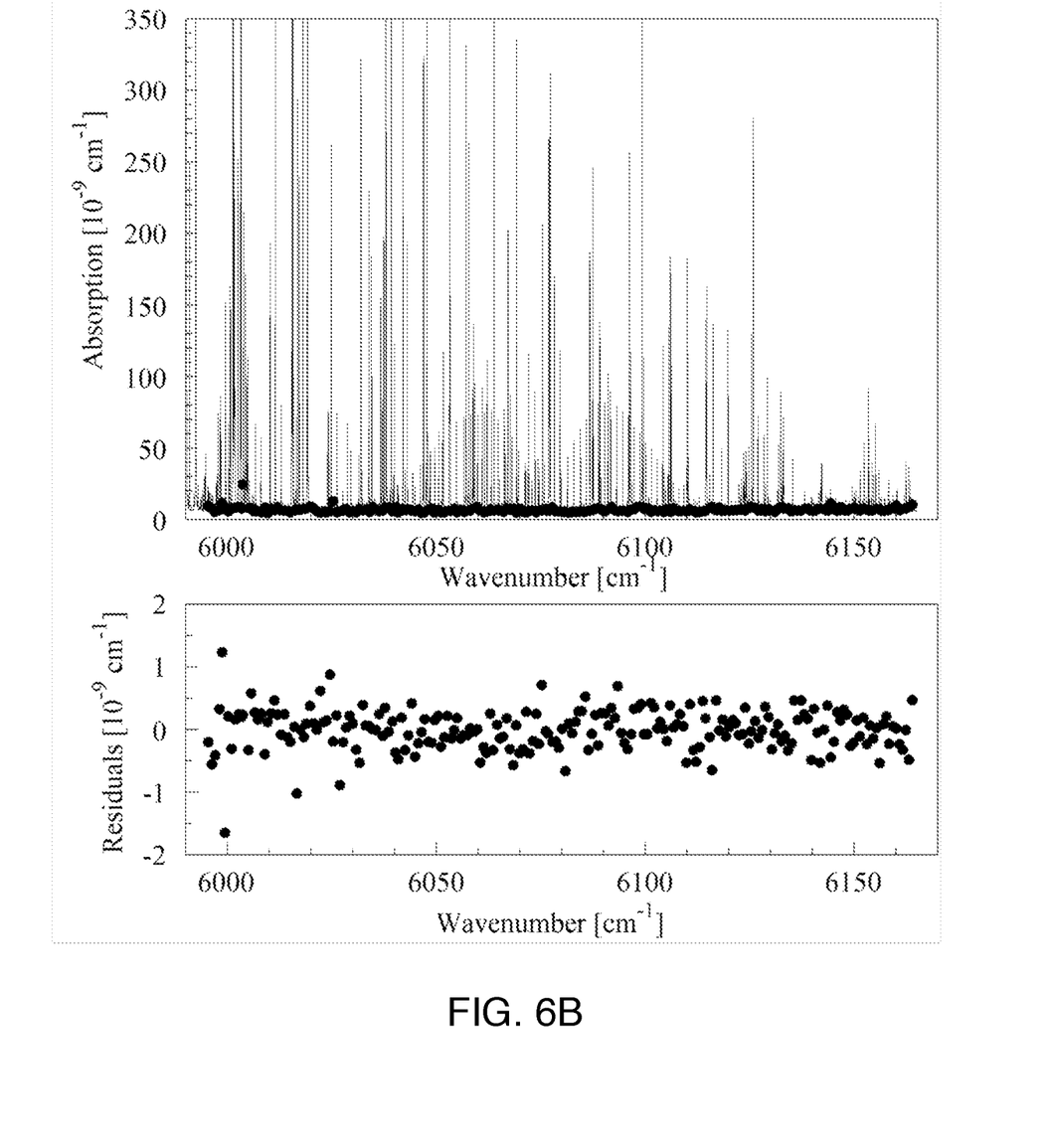

FIGS. 6A-B compare raw spectra of clean (nighttime) air acquired with the two schemes, where FIG. 6A uses equally spaced frequencies and FIG. 6B uses clutter avoidance. Upper plots on FIGS. 6A-B show the raw absorption data after subtracting the empty-cavity baseline (modeled as a quartic function). Note the difference in upper panel data point values between the regularly-spaced and clutter-avoiding spectra. Lower plots show the residuals of least-squares fits that include absorption by water vapor, $CO_2$, and methane (modeled as bisplines) as well as ammonia, acetic acid, isopropyl alcohol, and 1,1-difluoroethane (modeled as simple splines). Only the first three small molecules absorb to an extent that can be discerned by eye in these plots.

The regularly sampled spectrum (FIG. 6A) has numerous data points (solid black circles) for which the absorption coefficient is in the hundreds of ppb/cm, arising from absorption by strong water or methane lines. These are all absent from the data set that avoids clutter (FIG. 6B). The residuals of the fit to the clutter-free spectrum are noticeably smaller than for the regularly sampled spectrum. It would be premature to put too much emphasis on the residuals, since the magnitude of fit residuals depends crucially on the quality of the spectral model used in the fit, and it is likely that by expending more effort on the modeling of water and methane we could construct a more sophisticated model than the one used for this demonstration. Nevertheless, it is encouraging that this first exercise in avoiding clutter improves the spectral fitting when a simple spectral model is used.

The invention claimed is:

1. A method for performing spectroscopic analysis of a sample with an analysis instrument, the method comprising:
  for a predetermined frequency range and one or more predetermined clutter species, automatically determining one or more avoidance intervals in the predetermined frequency range;
  performing spectroscopy of one or more analyte species in the sample at a first set of frequencies that are all outside the avoidance intervals to provide a first set of data points; and
  wherein the analyte species are distinct from the clutter species.

2. The method of claim 1, wherein the one or more clutter species include methane, carbon dioxide and water vapor.

3. The method of claim 1, wherein the first set of frequencies are selected to improve a spectral fitting of the one or more analyte species.

4. The method of claim 1, further comprising spectral fitting of off-resonance clutter features in the first set of data points to improve sensitivity to the one or more analyte species.

5. The method of claim 4, further comprising performing spectroscopy of the sample to provide a second set of data points.

6. The method of claim 5, wherein the second set of data points provides improved spectral fitting of the off-resonance clutter features in the first set of data points.

7. The method of claim 6, wherein the improved spectral fitting provides a reduction in one or more concentration uncertainties of one or more clutter species in the sample.

8. The method of claim 6, wherein the improved spectral fitting provides a reduction in one or more isotopologue abundance uncertainties of one or more clutter species in the sample.

9. The method of claim 6, wherein the improved spectral fitting provides a spectral measurement of pressure of the sample.

10. The method of claim 6, wherein the improved spectral fitting provides a spectral measurement of temperature of the sample.

11. The method of claim 6, wherein the improved spectral fitting provides a spectral measurement of a background matrix gas composition of the sample.

12. The method of claim 11, wherein concentrations of one or more constituents of the background matrix gas composition are determined by their effect on spectral fitting of other chemical species using the first and/or second set of data points.

13. The method of claim 6, wherein the improved spectral fitting provides a reduction in uncertainties of one or more assigned frequency values in the first and/or second sets of data points.

14. The method of claim 1, wherein the analysis instrument is a cavity ring-down spectroscopy instrument configured for gas analysis.

15. The method of claim 14, wherein the first set of frequencies is determined by:
  providing values for minimum frequency ($v_{min}$) maximum frequency ($v_{max}$), and number of frequencies to sample (N) to define a sampled frequency range;
  automatically computing a nominal frequency separation from $v_{min}$, $v_{max}$, and N;
  automatically approximating the nominal frequency separation with a multiple of a free spectral range (FSR) of an optical cavity of the cavity ring-down spectroscopy instrument to provide a frequency spacing $\Delta v$;
  automatically determining a set of preliminary frequencies to cover the sampled frequency range with a comb of frequencies spaced by $\Delta v$ and including a reference frequency $v_0$; and
  automatically adjusting frequencies in the set of preliminary frequencies to avoid the avoidance intervals to provide the first set of frequencies.

16. The method of claim 15, wherein the automatically adjusting frequencies in the set of preliminary frequencies comprises, for each preliminary frequency inside an avoidance interval:
  automatically shifting the preliminary frequency by a multiple M of the FSR to move it outside any avoidance interval;
  wherein M is minimized individually for each shifted frequency.

17. The method of claim 1, wherein the automatically determining one or more avoidance intervals in the predetermined frequency range comprises:
  providing spectral data of the one or more predetermined clutter species at a set of reference frequencies in the predetermined frequency range;
  automatically flagging reference frequencies having clutter absorption values greater than a predetermined threshold; and
  automatically defining the avoidance intervals as contiguous sets of flagged reference frequencies.

18. The method of claim 17, wherein a spacing of the reference frequencies is less than a full-width half maximum line width of any spectral feature of any of the predetermined clutter species.

* * * * *